(12) United States Patent
Yamaguchi et al.

(10) Patent No.: US 11,145,402 B2
(45) Date of Patent: Oct. 12, 2021

(54) THERAPY ASSISTANCE SYSTEM AND THERAPY ASSISTANCE PROGRAM

(71) Applicant: Psychic VR Lab Co., Ltd., Tokyo (JP)

(72) Inventors: Masahiro Yamaguchi, Tokyo (JP); Masayo Matsumura, Tokyo (JP); Hikari Shimada, Osaka (JP); Kenji Araki, Hokkaido (JP)

(73) Assignee: Psychic VR Lab Co., Ltd., Tokyo (JP)

( * ) Notice: Subject to any disclaimer, the term of this patent is extended or adjusted under 35 U.S.C. 154(b) by 0 days.

(21) Appl. No.: 16/709,762

(22) Filed: Dec. 10, 2019

(65) Prior Publication Data

US 2020/0185080 A1 Jun. 11, 2020

(30) Foreign Application Priority Data

Dec. 11, 2018 (JP) .............................. JP2018-232027

(51) Int. Cl.
*G16H 20/70* (2018.01)
*G02B 27/01* (2006.01)
(Continued)

(52) U.S. Cl.
CPC ............ *G16H 20/70* (2018.01); *G02B 27/017* (2013.01); *G06T 19/006* (2013.01); *G06T 19/20* (2013.01); *G06T 2210/41* (2013.01)

(58) Field of Classification Search
CPC ... G06T 19/006; G06T 19/20; G06T 2210/41; G02B 27/017; G16H 20/70
See application file for complete search history.

(56) References Cited

U.S. PATENT DOCUMENTS

| 2015/0084850 A1* | 3/2015 | Kim | ..................... G02B 27/644 345/156 |
| 2016/0156850 A1* | 6/2016 | Werblin | ............... G02B 27/017 348/63 |

(Continued)

FOREIGN PATENT DOCUMENTS

| JP | 2017-189591 A | 10/2017 | |
| JP | 6416338 B1 * | 10/2018 | |
| WO | WO-2018069570 A1 * | 4/2018 | ............... G06T 7/20 |

OTHER PUBLICATIONS

Yamaguchi et al., Psychological Effect of Telescope Virtual Screens using VR Headset, Sep. 19, 2018, IEEE, In 2018 9th International Conference on Awareness Science and Technology (iCAST), pp. 175-178. (Year: 2018).*

(Continued)

*Primary Examiner* — Jeffery A Brier
(74) *Attorney, Agent, or Firm* — Kratz, Quintos & Hanson, LLP

(57) ABSTRACT

A therapy assistance system includes: a display device 1 configured to be mounted on a head and configured to display an image; and a control device configured to reproduce the image on the display device. The control device includes: a content storage means configured to store image content to be reproduced on the display device; and a rendition process means configured to perform a rendition process on the image content to be reproduced, which is loaded from the content storage means, so as to display the image content on the display device as an image in a virtual reality space. The rendition process means includes an FOV control means configured to perform control so as to narrow a field of view (FOV) for an image to be reproduced.

2 Claims, 8 Drawing Sheets

(51) Int. Cl.
  *G06T 19/00*  (2011.01)
  *G06T 19/20*  (2011.01)

(56) References Cited

U.S. PATENT DOCUMENTS

2018/0096517 A1* 4/2018 Mallinson ................ G06N 3/08
2018/0328697 A1* 11/2018 Sampat .................... F41G 5/24
2019/0141252 A1* 5/2019 Pallamsetty ....... H04N 5/23238

OTHER PUBLICATIONS

Yamaguchi et al., Emotional Evaluation for Images Displayed with Different Type of Screens in Virtual Reality Headset, Jan. 18, 2018, In Proceedings of The Twenty-Third International Symposium on Artificial Life and Robotics 2018, pp. 557-560. (Year: 2018).*
M. Meehan, et al.; "Effect of Latency on Presence in Stressful Virtual Environments"; 2003; pp. 141-148 (8 sheets).

* cited by examiner

THERAPY ASSISTANCE SYSTEM AND THERAPY ASSISTANCE PROGRAM

FIELD OF THE INVENTION

The present invention relates to a therapy assistance system employing an image displaying technology.

DESCRIPTION OF THE BACKGROUND ART

In recent years, inexpensive and high-quality virtual reality (VR) head-mounted displays (VR-HMDs) have become widespread and used for various purposes. In addition, researches have been in progress regarding management of anxiety and pain with use of VR, in NON-PATENT LITERATURE 1, influence of VR on psychological factors regarding pain relief was analyzed, and the analysis led to the conclusion that the sense of presence, joy, and anxiety influence pain relief. Previous researches indicate that VR has influenced our emotions and bodies and has functioned, for patients, as an efficient tool for managing anxiety and pain.

However, such functions are each greatly dependent on the type of content. For example, if a snow-related type of content is shown to a patient who has suffered a burn, the content favorably functions as a tool for mitigating the pain. Meanwhile, it is effective to show animation intended for children to a child patient. The inventor of the present invention previously proposed such a tool (see Patent Literature 1).

CITATION LIST

Patent Literature

[PTL 1] Japanese Unexamined Patent Application Publication No. 2017-189591

NON-PATENT LITERATURE

[NPL 1] Meehan, M., Razzaque, S., Whitton, M. C., & Brooks, F. P. (March, 2003), "Effect of Latency on Presence in Stressful Virtual Environments", in Proceedings of the IEEE Virtual Reality 2003 (p 141-148)

SUMMARY OF THE INVENTION

Problem to be Solved by the Invention

In consideration of the above-described circumstances, an object of the present invention is to provide a therapy assistance system capable of mitigating a sensation such as pain, a way of thinking such as negative thinking, and an emotion, regardless of the type of image content, thereby being capable of facilitating therapy.

Means to Solve the Problem

The present inventor focused on the field of view (FOV), searched for effective emotional responses dependent on neither hardware nor content, and conducted "1. Emotional Evaluation Experiment" and "2. HMD Stability Evaluation Experiment" in EXAMPLES described later. As a result, it was found that the emotional responses were more greatly influenced in a virtual telescope screen environment with a narrowed FOV than in a normal case. In particular, according to "2. HMD Stability Evaluation Experiment", the attentions of subjects indicated in the results of the "1. Emotional Evaluation Experiment" were paid to the screen. Accordingly, it was conceived that narrowing of the FOV as described above allows consciousness to be more intensely guided to and concentrated on an image, and thus a sensation such as pain, a way of thinking such as negative thinking, and an emotion can be mitigated, whereby therapy is also facilitated. Thus, the present invention has been completed.

Specifically, the present invention encompasses the following features.

(1) A therapy assistance system employing an image displaying technology, the therapy assistance system being configured to show image content in a virtual reality space to a user so as to guide consciousness of the user to an image, thereby performing assistance in therapy, the therapy assistance system including: a display device configured to be mounted on a head of a user and configured to display an image; and a control device configured to reproduce the image on the display device, in which the control device includes a content storage means configured to store image content to be reproduced on the display device, and a rendition process means configured to perform a rendition process on the image content to be reproduced, which is loaded from the content storage means, the rendition process means performing the rendition process so as to display the image content on the display device as an image in the virtual reality space, and the rendition process means includes an FOV control means configured to perform control so as to narrow a field of view (FOV) for an image to be reproduced.

(2) The therapy assistance system according to (1) further including a manipulation means through which an operation of the FOV control means is controlled.

(3) A therapy assistance program configured to cause a computer to function as each means of the control device of the therapy assistance system according to (1) or (2), the program being configured to cause the computer to function as: the content storage means configured to store image content to be reproduced on the display device; and the rendition process means configured to perform a rendition process on the image content to be reproduced, which is loaded from the content storage means, the rendition process means performing the rendition process so as to display the image content on the display device, the rendition process means including the FOV control means configured to perform control so as to narrow the FOV for an image to be reproduced.

According to the present invention, when image content in the virtual reality space is shown by the display device mounted on the head, the FOV for an image to be reproduced is controlled so as to be narrowed. This narrowing causes the sight in the VR to adapt more responsively to the movement of the display device on the head, and thus the user mounted with the display device inevitably concentrates so as not to move the head in order to appropriately view the target image. Accordingly, the consciousness is more intensely guided to and concentrated on the image and thus a sensation such as pain, a way of thinking such as negative thinking, and an emotion are mitigated, regardless of the type of image content. Therefore, therapy can be facilitated.

DESCRIPTION OF THE PREFERRED EMBODIMENTS

Next, an embodiment of the present invention will be described in detail with reference to the appended drawings.

Figure 1:
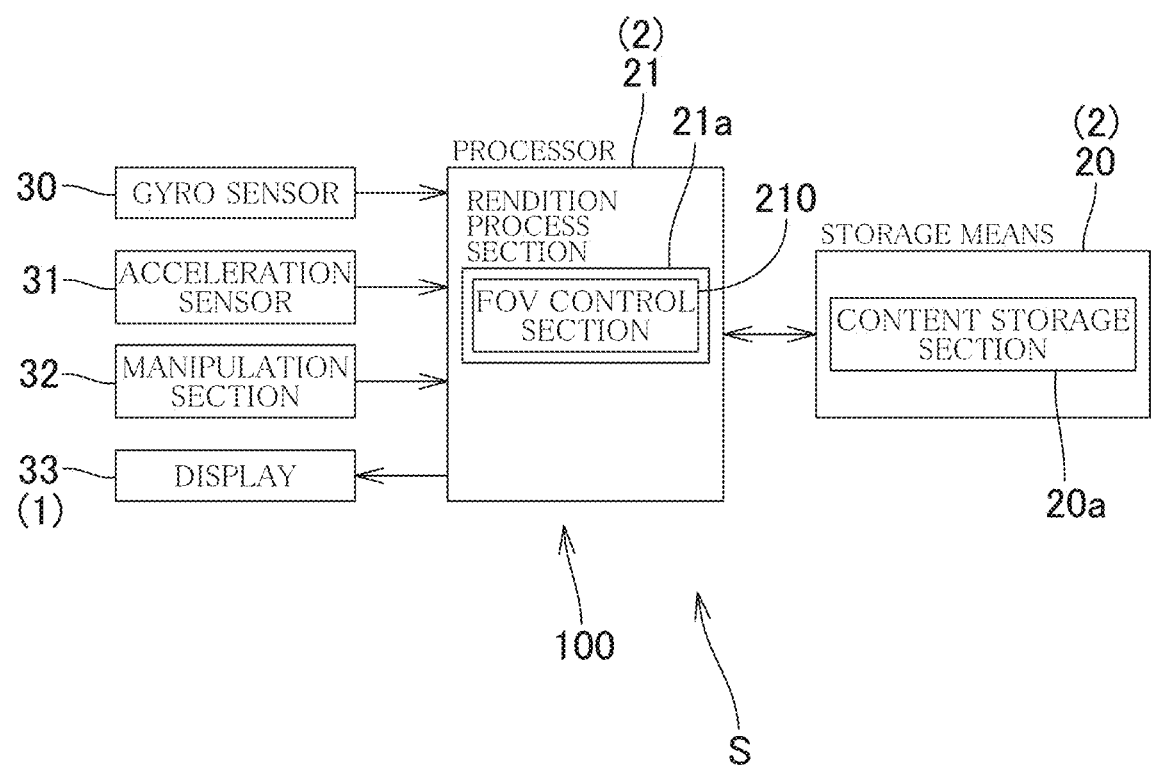
FIG. 1 is a block diagram showing a configuration of a therapy assistance system according to a representative embodiment of the present invention.

As shown in FIG. 1, a therapy assistance system S of the present invention includes: a display device 1 which is mounted on the head of a user and displays an image; and a control device 2 which reproduces the image on the display device. The display device 1 is implemented by a display of a VR-HMD 100. The control device 2 is implemented by a computer that is composed of a storage means 20 and a processor 21 and that is a controller included in the VR-HMD.

The storage means 20 is implemented by, for example, a storage memory such as a RAM or a ROM inside or outside the processor 21. The storage means 20 stores processed data and a program that specifies procedures of various process operations to be performed by the processor 21. The storage means 20 may be, for example, a solid-state drive (SSD) which is a storage medium that mainly uses a flash memory. However, the storage means 20 is not limited thereto. The storage means 20 includes a content storage section 20a which stores image content to be reproduced on the display device 1. The storage means 20 is used also as the location for storing various other data regarding an operation system, settings, and use.

The processor 21 is composed mainly of a CPU or a GPU such as a microprocessor, and allows various information to be transmitted and received among a gyro sensor 30, an acceleration sensor 31, a manipulation section 32, a display 33, and the like through an input/output section and a bus line. The processor 21 has, as a functional component, a rendition process section 21a which performs a rendition process on the image content to be reproduced that is loaded from the content storage section 20a of the storage means 20, the rendition process section 21a performing the rendition process so as to display the image content on the display device 1 as an image in a virtual reality space. The rendition process section 21a includes an FOV control section 210 which performs control so as to narrow a field of view (FOV) for an image to be reproduced. These functions are realized by the above-described program.

If the FOV is narrowed by the FOV control section 210, the visual-field angle becomes small, and the viewpoint in the VR is as if the user looks through a telescope. Thus, when the HMD is moved, the sight is greatly shifted. That is, if the FOV is narrowed, the sight in the VR adapts more responsively to the movement of the HMD. Accordingly, the user mounted with the HMD needs to continuously concentrate so as not to move the head in order to appropriately view the target image, resulting in consciousness being guided to and concentrated on the image. The therapy assistance system S of the present invention enables the consciousness to thus be guided to and concentrated on the image, and thus is capable of mitigating a sensation such as pain, a way of thinking such as negative thinking, and an emotion, thereby being capable of facilitating therapy.

It is assumed that the FOV control section 201 controls the FOV in accordance with a manipulation performed through the manipulation section 32 by a physician, a dentist, or the like. The FOV control section 201 performs control so as to narrow the FOV in accordance with an instruction from the manipulation section 32. The value of the FOV may be changed from a normal value to a predetermined small value. Alternatively, the manipulation section 32 may be configured with a dial or the like, and an instruction may be given on the basis of the value indicated by the dial or the like. The time period during which the value of the FOV is kept at a small value, may be set to a predetermined time period in advance. In this case, it is preferable that the time period can be set with the manipulation section. In addition, the value of the FOV may be set in advance to be intermittently reduced by means of the program, in accordance with an instruction from the manipulation section 32.

Although the image content is not particularly limited, animation, an attraction image, or the like in Which a patient is keenly interested is preferable. Since the patient shifts his/her consciousness from the therapy so as to concentrate on such image content, a dentist can smoothly proceed with the therapy. In particular, while a therapy that causes pain is being operated, manipulation for the FOV is performed through the manipulation section 32 so as to cause the consciousness to be more concentrated on the image content, whereby less pain is perceived.

The manipulation section 32 may be a physical switch, a touch panel, or the like. The manipulation section 32 may be integrated with the HMD 100, or may be a remote-control switch or the like that is connected to the HMD through a wire or wirelessly. Alternatively, the manipulation section 32 may be implemented, as in modifications described later, by a manipulation section of a personal computer or an auxiliary device (controller) that is, in the same manner, connected to the HMD through a wire or wirelessly and manipulated by a physician or a dentist.

Figure 2A:
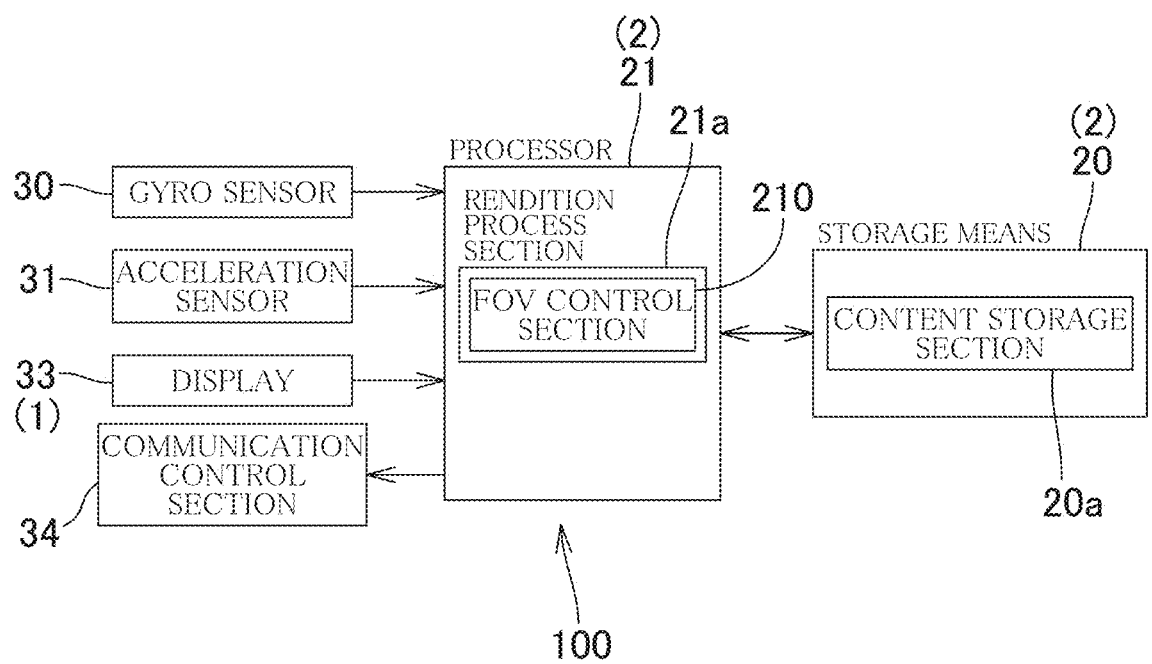
FIG. 2A and FIG. 2B are block diagrams showing a modification of the therapy assistance system.
Figure 2B:
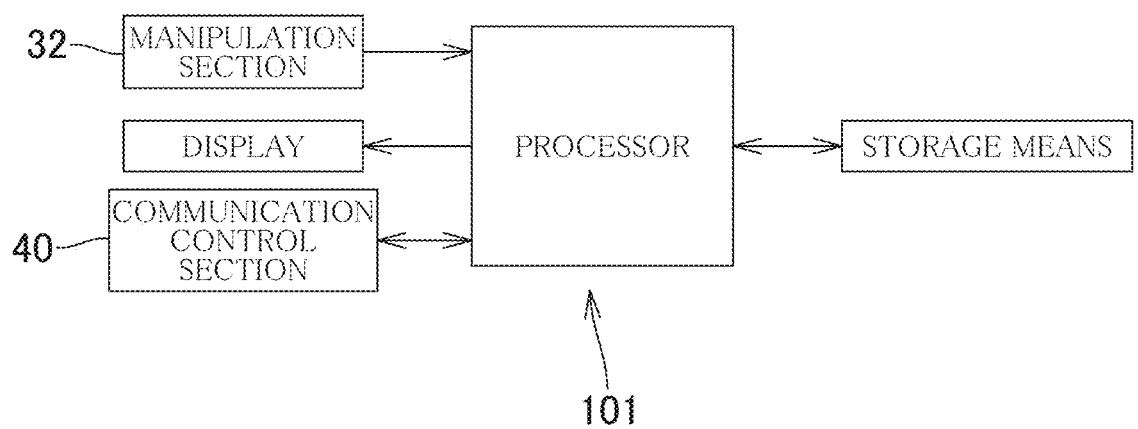

FIG. 2A and FIG. 2B show a modification of the system provided with a personal computer 101 which is connected to the HMD 100 through a wire or wirelessly and which is manipulated by a physician or a dentist. A general-purpose computer can be used as the personal computer 101. The personal computer 101 includes: a processor such as a general CPU; a storage means such as a memory or a hard disk; a manipulation section such as a mouse or a keyboard; a display; and so on.

Besides the above components, communication control sections 34 and 40 are respectively provided to the HMD 100 and the personal computer 101 so as to perform data communication therebetween. The communication control sections 34 and 40 enable connection through wired or wireless local area network (LAN), Bluetooth, infrared communication, or the like. A physician-side information communication terminal 3 may be a smartphone, a tablet, or the like instead of the personal computer. In this example, not only the manipulation section 32 is implemented by the manipulation section 32 of the personal computer 101, but also, for example, the rendition process section 21a and the FOV control section 210 may be provided to the processor of the personal computer 101.

Figure 3A:
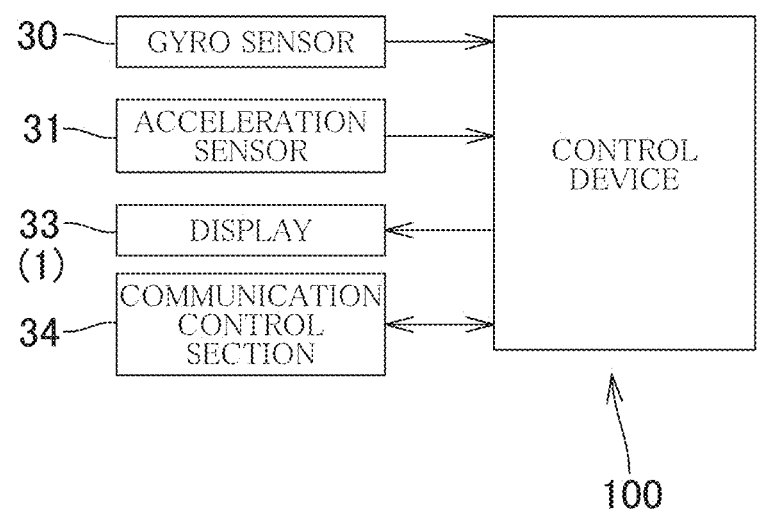
FIG. 3A and FIG. 3B are block diagrams showing another modification of the therapy assistance system.
Figure 3B:
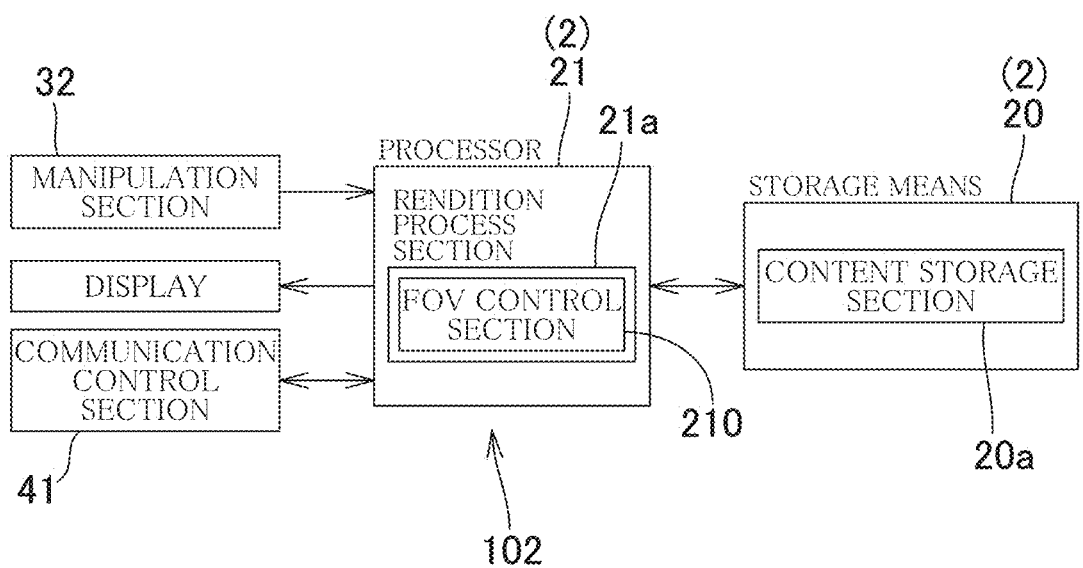

FIG. 3A and FIG. 3B show a modification of the system provided with an auxiliary device (controller) 102 which is connected to the HMD 100 through a wire or wirelessly. As shown in FIG. 3B, the auxiliary device 102 includes the manipulation section 32 and the control device 2 which is composed of the above-described storage means 20 and processor 21. The same components are denoted by the same reference characters, and description thereof is omitted. Besides the above components, communication control sections 34 and 41 are respectively provided to the HMD 100 and the auxiliary device 102 so as to perform data communication therebetween. The communication control sections 34 and 41 enable connection through wired or wireless local area network (LAN), Bluetooth, infrared communication, or the like.

Alternatively, another modification may be employed in which not only the display device 1 and the control device 2 are provided to a casing of the HDM, but also parts of the HDM (in particular, the display device 1 and the control device 2) may be implemented, as in common practice, by a portable device having a function of a multifunctional portable phone (smartphone) or a function similar to that of the multifunctional portable phone. In this case, the display device 1 is a display of the portable device, and the function of the control device 2 is performed by a control device of the portable device The therapy assistance system S of the present invention controls the FOV for an image to be reproduced in the VR, so that a patient viewing the image is caused to concentrate on the image content, whereby pain can be mitigated, and thus assistance in the therapy can be performed. The therapy assistance system S is not limited in use to dentistry including dental general practice, pediatric dentistry, orthodontics, and oral surgery, but can be effectively used for, for example, therapies in the fields of overall medical care that broadly encompasses otorhinolaryngology, internal medicine, surgery, and so on.

The embodiment of the present invention has been described above. However, the present invention is by no means limited to this embodiment, and can be implemented, as a matter of course, in various forms without departing from the gist of the present invention.

EXAMPLES

1. Emotional Evaluation Experiment

An experiment was conducted to study emotional effects in virtual screen environments (of a normal screen with an FOV of 108° and a telescope screen with an FOV of 2°) different from each other in FOV with use of the International Affective Picture System (IAPS) and the Self-Assessment Manikin (SAM).

(Experiment Method)
(Subject)

12 volunteers (nine males and three females) participated in the experiment as subjects. The ages ranged from 21 to 61.

(Virtual Screen Environments)
See Table 1.

TABLE 1

|  | Screen size (m) | FOV (°) | Distance (m) |
|---|---|---|---|
| Normal | 8 × 6 | 108 | 4 |
| Telescope | 8 × 6 | 2 | 1,200 |

Figure 4:
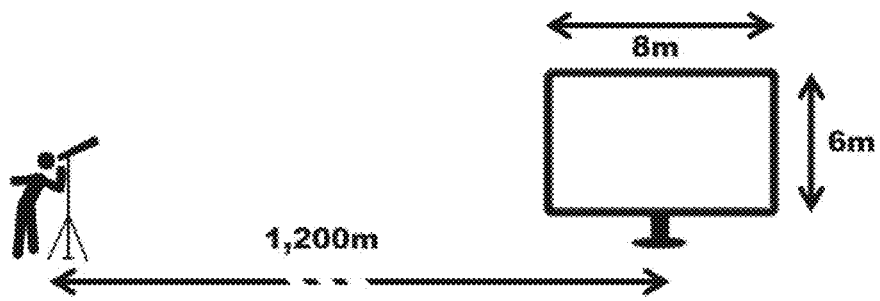
FIG. 4 is a schematic diagram for explaining a telescope screen environment in an emotional evaluation experiment.
Figure 5:
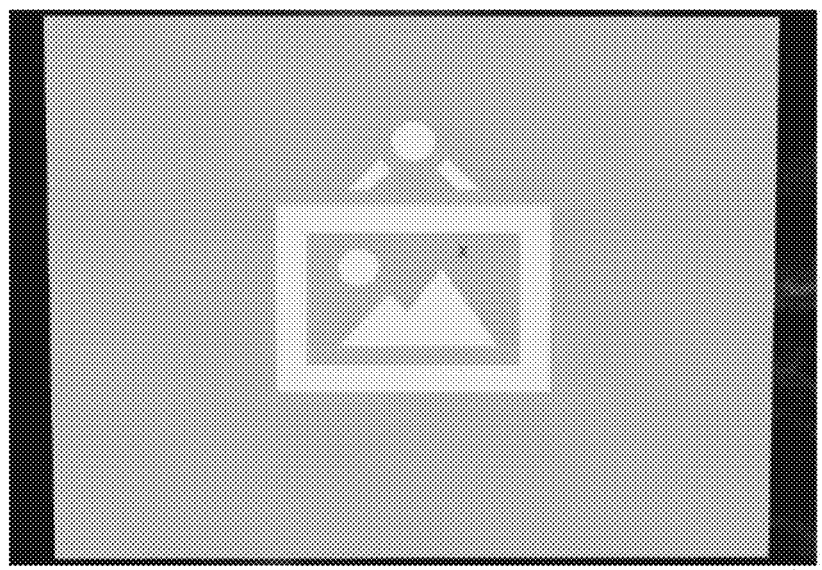
FIG. 5 is a simplified diagram of a picture displayed in the emotional evaluation experiment.

In the virtual environment, both screens were square flat screens each having a size of 8×6 m and were displayed in approximately the same size. The normal screen was located away from the eyes by 4 m, and the FOV of a virtual camera was set to 108°. This environment was similar to an environment in which an actual screen having a size of 8×6 m was located away from a subject by 4 m. The telescope screen included a virtual camera having an FOV of 2°, and was located away from the eyes by 1200 m in the virtual environment. That is, this telescope screen environment functioned like a telescope with a screen being at a distance of 1200 m from a subject. FIG. 4 is a schematic diagram of the virtual screen environment of the telescope screen. FIG. 5 illustrates an example of the manner of display of an IAPS picture visualized on the HMD, (HMD)

A smartphone-based HMD was composed of a 5.8-inch smartphone and a cardboard-type VR component kit. The MID was connected to a personal computer (PC), and the PC controlled content on the HMD and recorded logs of the experiment. Monocular lens goggles were used for the HMD.

(Self-Assessment Manikin (SAM))

Figure 6:
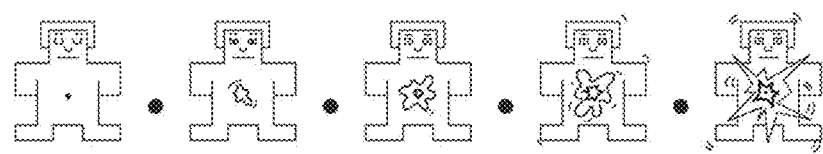
FIG. 6 is an explanatory diagram showing the Self-Assessment Manikin used in the emotional evaluation experiment.

The SAM was developed by Lang, P. J. and is used for evaluating emotional responses of subjects. The SAM is a graphic scale with a cartoon-like character, and is a nonverbal assessment technique that is widely used for measuring pleasure, arousal, and dominance. FIG. 6 shows a Self-Assessment Manikin (SAM) scale for arousal. Five manikin images (FIG. 6) for evaluation were set, and the intermediate positions between the manikins were selectable by the subjects, as intermediate levels, That is, this scale was prepared for measuring the arousal level with use of a total of nine scales. Each subject selected one of the levels each time the screen appeared on the HMD.

(Pictures)

Pictures used in the experiment were selected from picture data sets of the International Affective Picture System (IAPS). All the pictures in the IAPS are assessed in terms of pleasure/displeasure, arousal level, and dominance level. The IAPS has been widely used as a picture database that is designed for showing a series of standardized pictures for studying emotions and attention in psychologic researches. For evaluation regarding arousal, 20 pictures were selected from among highest-evaluation pictures, and 20 pictures were selected from among lowest-evaluation pictures. The two groups of pictures are defined as an "intense" group and a "normal" group. The pictures in the intense group were expected to stimulate emotions of the subjects, whereas the pictures in the normal group were expected to keep the emotions of the subjects calm.

Specifically, the pictures assigned with the following IAPS numbers were used in the experiment.

Pictures in the normal group: 2190, 2840, 3170, 5130, 5740, 5800, 7000, 7004, 7006, 7010, 7020, 7031, 7060, 7080, 7110, 7187, 7217, 7490, 7491, and 7950

Pictures in the intense group: 3000, 3010, 3060, 3069, 3080, 3170, 4220, 4290, 4668, 4800, 5621, 6230, 6350, 6550, 8030, 8179, 8185, 8492, 9410, and 9940

Numbers assigned to injury pictures among the intense pictures are 3000, 3010, 3060, 3069, 3080, and 3170.

(Software)

Software for the experiment was installed in the smartphone, and the smartphone was attached to the goggles used for the VR-HMD. The images randomly selected from the lists were each displayed after a countdown on the virtual screen of the HMD.

The FOV of the virtual camera also randomly changed, and the relationship between the FOV and the emotional response was recorded.

The software randomly selects the type of the virtual screen (the normal screen or the telescope screen) and a picture to be displayed. Either of the two types of virtual screens, i.e., the "normal" screen or the "telescope" screen, was selected with a probability of 50%, and either of the two picture set groups, i.e., the "intense" group or the "normal" group, was also selected with a probability of 50%. The software randomly selected, from the selected picture set group, a picture to be displayed. The selected type of the virtual display was used for displaying, in the HMD, the picture selected by the software.

(Experiment Procedure)

Each subject put on acoustic ear pads to reduce ambient noise while using the VR-HMD. Although the summary and the procedure of the experiment were explained to the subject, neither the expected result nor the purpose was explained to the subject. The subject was told that an unpleasant picture might appear on the screen and that the experiment might be interrupted if the subject felt unpleasant, One session consisted of 20 pictures being displayed. In the session, loading images were each displayed for 8 to 13 seconds and the pictures were each displayed for 6 seconds. After each picture disappeared, the subject indicated an arousal level with use of an SAM image. The type of the picture, the type of the screen, and the arousal level were recorded along with the image and the subject number.

(Results and Consideration)

Figure 7A:
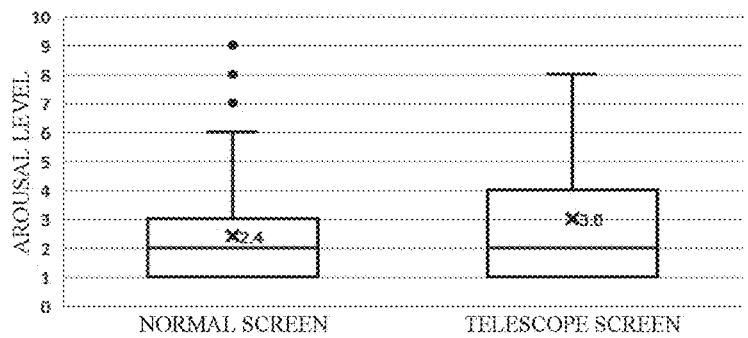
FIG. 7A to FIG. 7C are charts indicating arousal levels in the emotional evaluation experiment.
Figure 7B:
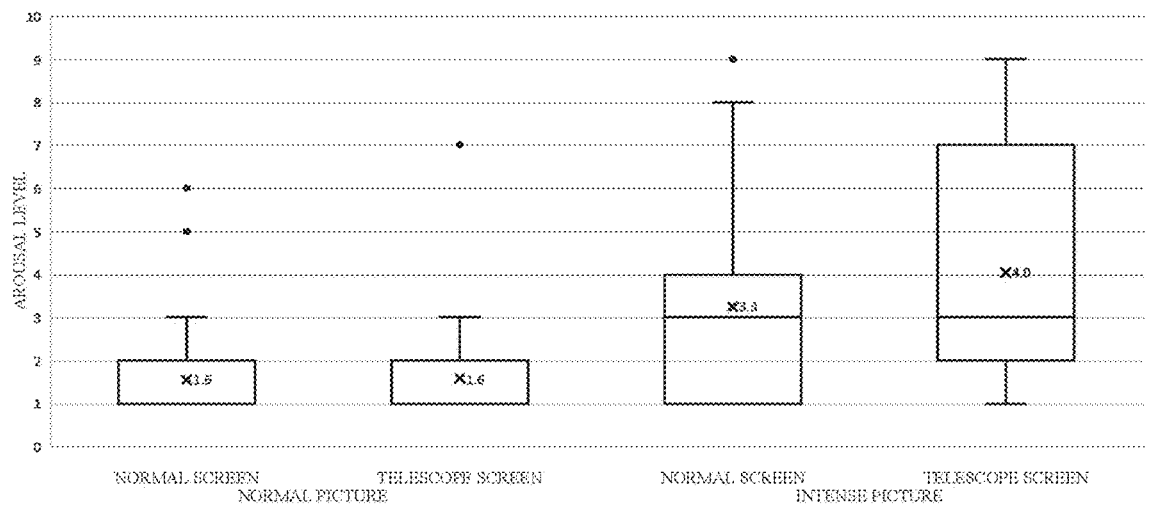
Figure 7C:
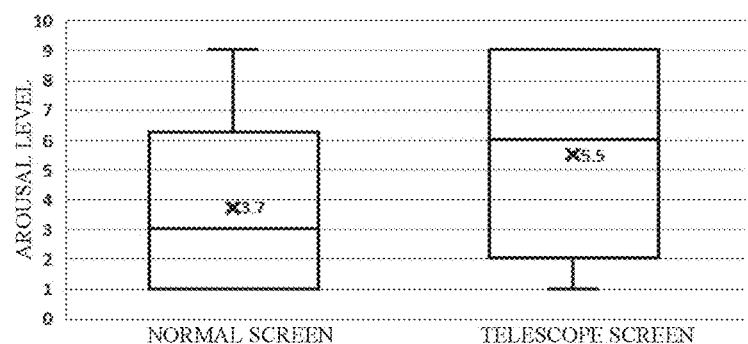

FIG. 7A to FIG. 7C each show a box and whisker chart for the arousal levels indicated with use of the Self-Assessment Manikin (SAM).

Table 2 indicates statistics of the recorded arousal levels for sets of the selected picture data.

TABLE 2

| Picture data set | Normal screen (FOV: 108°) | | | Telescope screen (FOV: 2°) | | | F-test result | t-test result |
|---|---|---|---|---|---|---|---|---|
| | Number of samples (n) | Mean value (M) | Standard deviation (SD) | Number of samples (n) | Mean value (M) | Standard deviation (SD) | | |
| All pictures | 120 | 2.4 | 2.0 | 107 | 3.0 | 2.6 | $F(119, 106) = 0.73, P = 0.05$ | $t(196) = 1.65, p = 0.05$ |
| Normal pictures | 61 | 1.6 | 0.9 | 45 | 1.6 | 1.0 | $F(60, 44) = 0.63, P = 0.05$ | $t(104) = 1.66, p = 0.05$ |
| Intense pictures | 59 | 3.3 | 2.3 | 62 | 4.0 | 2.9 | $F(61, 58) = 0.65, P = 0.05$ | $t(119) = 1.66, p = 0.05$ |
| injury pictures | 22 | 3.7 | 2.8 | 17 | 5.5 | 3.2 | $F(21, 16) = 0.46, P = 0.05$ | $t(37) = 1.69, p = 0.05$ |

Emotional responses of the 12 subjects were recorded for a total of 227 times of display. Two of the subjects had their sessions stopped at the 11$^{th}$ and 18$^{th}$ displays because of displeasure. It is found that influence of being in the telescope screen environment is less for the normal pictures, whereas the influence of being in the telescope screen environment is greater for the intense pictures and the injury pictures. In addition, the t-test result obtained with all the picture data sets indicates that the subjects feel more arousal when viewing the pictures in the telescope screen environment. Furthermore, it is found that, in the normal screen, the type of pictures—whether the normal pictures or the intense pictures—does not significantly affect emotional responses.

2. HMD Stability Evaluation Experiment

Next, an experiment was conducted in which the stability of the HMD was assessed so as to check the degree of concentration in the telescope screen.

In the above-described "1. Emotional Evaluation Experiment", the subjects moved, in many cases, the HMD when staggering pictures appeared. Therefore, the stability of the HMD was tested by the type of the screen (normal screen/telescope screen) in the present experiment. To this end, video content was used instead of the IAPS pictures in the present experiment in which the same video data was shown to all subjects in both the normal screen and the telescope screen.

(Experiment Method)

(Subjects)

12 volunteers (five males and seven females) participated in the experiment as subjects, and the ages ranged from 15 to 52.

(HMD)

A wearable HMD was composed of a 5.8-inch smartphone and a VR headset (ELECOM P-VR1G01WH) unlike in the above-described "1. Emotional Evaluation Experiment" in which the cardboard-type HMD was used while being held with hands. The video content was played for 100 seconds from a connected PC.

(Software)

The playing of the video and the type of the screen were controlled by specified software, and the physical stability of the HMD was recorded by the software. The software accurately recorded, in a longitudinal axis and a lateral axis, the rotational angle of the HMD at 10 Hz with use of a gyroscope sensor of the smartphone-based HMD. When each subject tilted the HMD to a certain degree, the rotational angle from the initial position was saved in a log file. The recording was performed with the rotational angle about the vertical axis being defined as X and the rotational angle about the horizontal axis being defined as Y. The type of the screen (normal screen/telescope screen) was changed up to ten times during 100 seconds, and 1000 points of data were recorded for analyzing the stability.

(Experiment Procedure)

The present experiment was conducted under the same condition as that of the above-described "1. Emotional Evaluation Experiment". The only difference therefrom was that the subjects did not wear any acoustic earmuffs during the present experiment since the subjects viewed the video with audio. The subjects were instructed to view the video for 100 seconds with the HMD, but did not receive any other information. Information about the stability and the type of the screen were recorded in a log file along with information about the subjects. The recorded data was analyzed after the experiment.

(Results and Observations)

Figure 8:
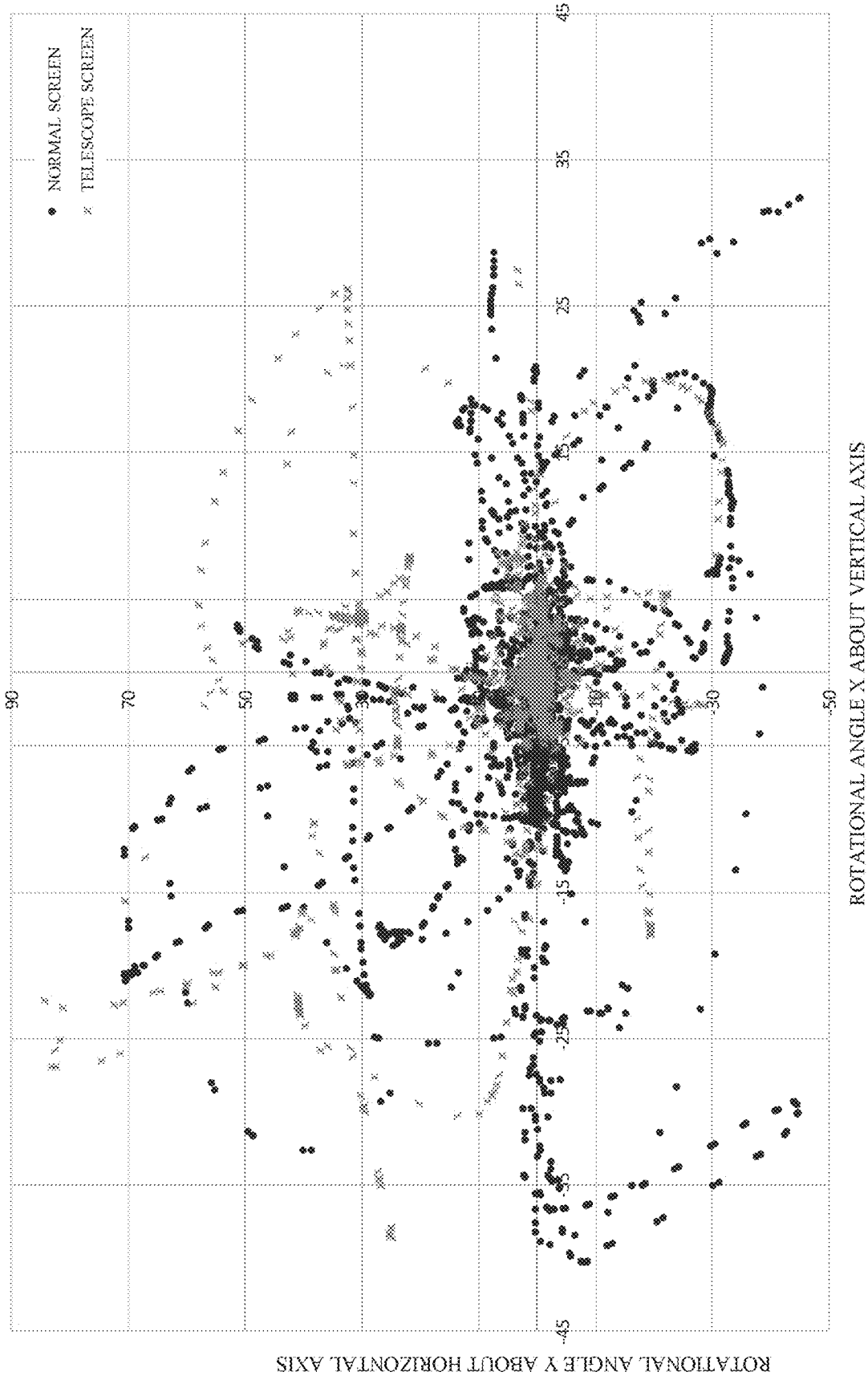
FIG. 8 is a data scatter diagram indicating the results of an HMD stability evaluation experiment.
Figure 9:
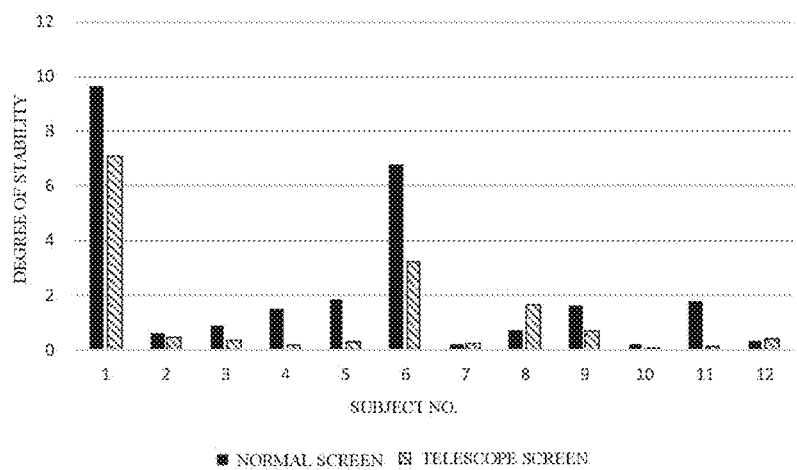
FIG. 9 is a graph indicating the results of the HMD stability evaluation experiment.

FIG. 8 is a scatter diagram of HMD angles in a total of 12000 pieces of recorded data from all the 12 subjects. X represents the rotational angle about the vertical axis, and Y represents the rotational angle about the horizontal axis. FIG. 9 is a graph indicating the amount of movement, in the normal and telescope screens, of each subject (a smaller amount indicates a higher stability). It is found that, when the video was viewed in the normal screen, the HMD was moved more than when the video was viewed in the telescope screen. Here, the result of the subject "8" is the reverse of this tendency. Since one great movement was observed for the subject in the telescope screen, it is considered that this exceptional movement caused the reversed result.

In Table 3, distances from the center of the plot are averaged for each type of the screen as indexes of the stability. Table 3 indicates that the value for the normal screen is not less than twice the value for the telescope screen.

TABLE 3

| Type of screen | Degree of stability of HMD |
| --- | --- |
| Normal | 3.0718 |
| Telescope | 1.5389 |

The stability of the HMD was calculated with the following Mathematical Expression 1 where $x_n$ and $y_n$ each represent an $n^{th}$ data piece among the recorded data pieces. A smaller value of the degree of stability indicates a higher stability.

$$\text{Stability} = \frac{1}{n}\Sigma\sqrt{x_n^2 + y_n^2} \qquad \text{[Mathematical Expression 1]}$$

3. Cold Press Test

Next, the results of a psychological experiment conducted through a cold press test with use of the telescope screen environment to analyze changes in the tolerance of each of subjects against pain, will be described. The cold press test is known as a standard test for evaluating the tolerance against pain through immersion of hands into cold water.

(Test Method)

(Subject)

14 volunteers (ten males and four females) participated in the experiment as subjects. The ages ranged from 25 to 52.

(HMD)

The wearable HMD same as that used in the above-described "2. HMD Stability Evaluation Experiment" was used, the HMD being composed of the 5.8-inch smartphone and the VR headset (ELECOM P-VR1G01WH).

(Software)

Figure 10:
FIG. 10 is a simplified diagram showing what can be seen in a picture displayed in a cold press test.

Software for the test was installed in the smartphone, and the smartphone was attached to the VR headset to obtain an HMD which was used as a VR-HMD. The VR-HMD was connected to a PC for controlling display on the VR-HMD according to data from a gyroscope of the VR-HMD. As shown in FIG. 10, the software displays a target marker and a sight marker in the YR. The field of view having been set was made available to the subjects as the telescope screen environment with an FOV of 2°.

(Test Procedure)

A wash bowl (φ315) was prepared and filled with water and ice before the experiment.

Each subject was asked to immerse one hand, and then the other hand, into the cold water in the wash bowl until the subject became unable to bear the pain. That is, the subject performed the immersion twice in total. Out of the two trials of immersion, one trial of immersion was performed while the VR-HMD (hereinafter, simply "HMD") in the telescope screen environment was mounted, and the other trial of immersion was performed while the HMD was not mounted. The order of presence and absence of the HMD and the order of the immersion of the hands (left hand/right hand), were each reversed between the subjects in order to avoid influence of the orders. The temperature of the water with the ice was kept at 0.4° C. in the experiment room. After each time of immersion, we waited for several minutes so as to keep the temperature at the same level in order to maintain the condition of the experiment. The duration until the subject put out each hand, was recorded as tolerance against pain. In addition, the recorded data was analyzed through a paired t-test in order to check whether or not the telescope virtual screen environment influenced the tolerance against pain.

When the HMD in the telescope screen environment was mounted during the immersion, the subject was asked to put a hand into the cold water while keeping the sight marker close to the target marker on the virtual screen. After feeling cold owing to the previous time of immersion, the subject took a sufficient rest for the next time of immersion until the subject no longer felt cold.

(Results and Consideration)

Figure 11:
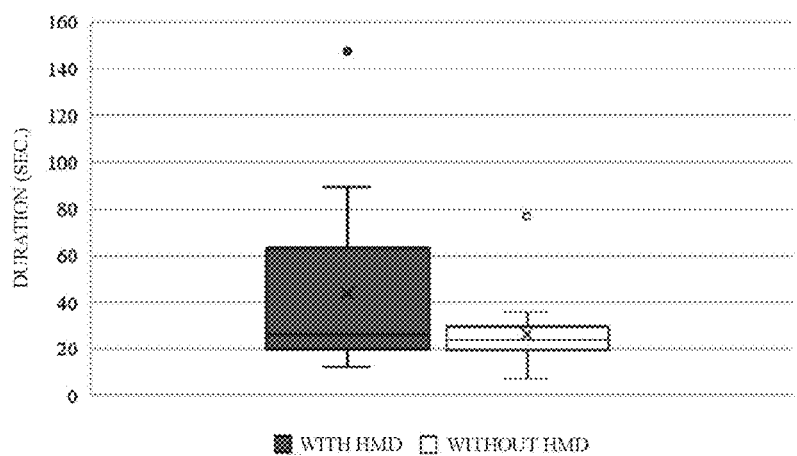
FIG. 11 is a chart indicating durations in the cold press test.
Figure 12:
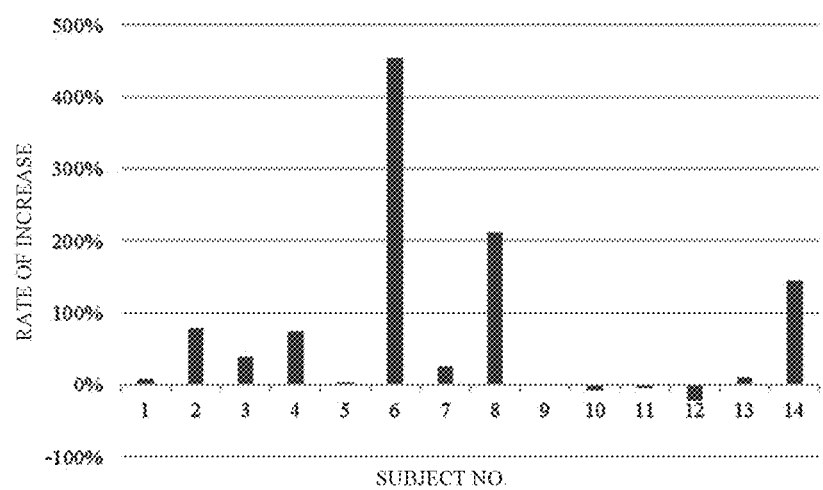
FIG. 12 is a graph indicating the results of the cold press test.

FIG. 11 is a box and whisker plot of the data. FIG. 12 is a plot indicating the rate of increase in the allowable time period of each subject in the case where the subject used the HMD. Table 4 indicates the recorded durations and data obtained by analysis.

TABLE 4

| Subject No. | With HMD | No HMD | With HMD/ No HMD |
|---|---|---|---|
| 1 | 83.30 | 76.80 | 1.08 |
| 2 | 17.20 | 9.60 | 1.79 |
| 3 | 32.60 | 23.40 | 1.39 |
| 4 | 12.30 | 7.10 | 1.73 |
| 5 | 24.70 | 23.90 | 1.03 |
| 6 | 147.40 | 26.60 | 5.54 |
| 7 | 39.30 | 31.40 | 1.25 |
| 8 | 89.40 | 28.70 | 3.11 |
| 9 | 21.40 | 21.30 | 1.00 |
| 10 | 22.90 | 24.70 | 0.93 |
| 11 | 21.00 | 22.00 | 0.95 |
| 12 | 27.90 | 36.00 | 0.78 |
| 13 | 15.90 | 14.40 | 1.10 |
| 14 | 56.30 | 23.10 | 2.44 |
| Mean value (sec.) | 43.69 | 26.36 | 1.66 |
| Scatter (sec.$^2$) | 1479.12 | 271.98 | |
| Pearson correlation | | 0.44 | |
| df | | 13 | |
| tStat | | 1.88 | |
| P(T <= t)one-tail | | 0.04 | $P < 0.05$ |

It is found from these results that the tolerance duration in the case where the HMD is used tends to be longer than the tolerance duration in the case where the HMD is not used. This finding indicates that the telescope screen environment allowed improvement in the tolerance against pain. As a result, it is found that the "pain" can be controlled through narrowing of the FOV of the VR-HMD. This method is dependent on neither hardware nor content, and thus is expected to be used in management of anxiety and pain, rehabilitation of those who suffer ADHD, medical preparation, and the like.

REFERENCE NUMERAL

S . . . Therapy assistance system
1 . . . Display device
100 . . . HMD
101 . . . Personal computer
102 . . . Auxiliary device (controller)
2 . . . Control device
20 . . . Storage means
20a . . . Content storage means
21 . . . Processor
21a . . . Rendition process means
210 . . . FOV control means
30 . . . Gyro sensor
31 . . . Acceleration sensor
32 . . . Manipulation section
33 . . . Display
34 . . . Communication control section
40 . . . Communication control section
41 . . . Communication control section

What is claimed is:

1. A therapy assistance system employing an image displaying technology, the therapy assistance system being configured to show image content in a virtual reality space to a user so as to guide consciousness of the user to an image, thereby performing assistance in therapy, the therapy assistance system comprising:
a display device mounted on a head of a user and displays an image, the image being responsive to the display device mounted on the head of the user;
a sensor device for detecting movement information of the display device mounted on the head of the user; and
a controller that reproduces the image on the display device, wherein
the controller includes:
a content storage that stores image content to be reproduced on the display device, and
a rendition processor that performs a rendition process on the image content to be reproduced, which is loaded from the content storage, the rendition processor performing the rendition process so as to display the image content on the display device as an image in the virtual reality space,
wherein the therapy assistance system further comprises a manipulator through which an operation of the FOV controller is controlled by an operator based on a desired FOV in the display device mounted on the head of the user in guiding the consciousness of the user to the image so as to assist in therapy,
wherein the rendition processor includes an FOV controller that narrows a field of view (FOV) for an image to be reproduced based on the desired FOV detected from the manipulator controlled by the operator, and
wherein the user moves based on the desired FOV detected from the manipulator controlled by the operator, movement information of the user being detected by the sensor device.

2. A non-transitory computer-readable medium storing a program having computer-executable instructions containing a therapy assistance program for causing a computer so as to control each section of the control device of the therapy assistance system according to claim 1, the program having the computer-executable instructions causing the computer to control:
the content storage to store image content to be reproduced on the display device; and the rendition processor to perform a rendition process on the image content to be reproduced, which is loaded from the content storage, the rendition processor performing the rendition process so as to display the image content on the display device, the rendition processor including the FOV controller that performs control so as to narrow the FOV for an image to be reproduced.

* * * * *